United States Patent [19]

Pflibsen et al.

[11] Patent Number: 4,856,891

[45] Date of Patent: Aug. 15, 1989

[54] EYE FUNDUS TRACKER/STABILIZER

[75] Inventors: Kent P. Pflibsen, Franklin; Michael T. Milbocker, Boston, both of Mass.

[73] Assignee: Eye Research Institute of Retina Foundation, Boston, Mass.

[21] Appl. No.: 14,994

[22] Filed: Feb. 17, 1987

[51] Int. Cl.$^4$ .............................................. A61B 3/10
[52] U.S. Cl. .................................... 351/210; 351/206; 351/211; 351/220; 351/246
[58] Field of Search ............... 351/206, 209, 210, 211, 351/220, 221, 246

[56] References Cited

U.S. PATENT DOCUMENTS

| | | |
|---|---|---|
| 4,257,688 | 3/1981 | Matsumura . |
| 4,443,075 | 4/1984 | Crane ..................... 351/209 |
| 4,579,430 | 4/1986 | Bille ...................... 351/206 |

FOREIGN PATENT DOCUMENTS 0167877  1/1986  European Pat. Off. .
61-5730 10/1977  Japan .

OTHER PUBLICATIONS

Confocal Scanning Laser Ophthalmoscope, Robert H. Webb and George W. Hughes to appear in Applied Optics, Special Fall 1986 Issue.
Ophthalmoscopie for Balayage Optique J. Cohen Saban et al., Innov. Tech Biol. Med.; vol. 5, No. 2, 1984, pp. 116–128 (translation supplied).

Primary Examiner—Rodney B. Bovernick
Assistant Examiner—Jay Patrick Ryan
Attorney, Agent, or Firm—Lahive & Cockfield

[57] ABSTRACT

An eye movement tracker for stabilizing in two dimensions a diagnostic, treatment or other ophthalmic illumination on the fundus has a laser source which produces a narrow directed tracking beam, an optical steering assembly for controllably directing the beam to illuminate a region of the fundus, and an optical imaging assembly for imaging the illuminated region on a spatially-distributed photodetecting element. A tracking circuit scans the detecting element to detect motion of a spatially variant intensity feature and controls the optical steering assembly to redirect the optical path and maintain the feature in a fixed position. This repositions the diagnostic or other illumination, maintaining it in a fixed position on the fundus during eye movement. Scanning rates many times those of conventional systems are achieved, effectively stabilizing even very rapid eye movements. A viewing port provides an operator with a 30 degree field of the subject's eye fundus.

21 Claims, 3 Drawing Sheets

EYE FUNDUS TRACKER/STABILIZER

This invention relates generally to instruments for tracking eye movements and to instruments for directing beams of light into the eye. In particular, the invention includes an electro-optical eye tracking and concatenated beam stabilizing system which fixes, by iterative corrections, the position on the fundus of a beam directed at the eye. The system for tracking eye movements described here involves the electro-optical tracking of retinal blood vessels and other structures with light absorption characteristics sufficiently different from the surrounding tissue of the eye fundus.

BACKGROUND

Applications requiring a beam fixed on a particular structure of the fundus to date have been hampered by the subject's normal eye movements. Uncontrolled eye movement introduces complications in such clinical treatments as laser photocoagulation. Thus a photocoagulation procedure could be improved using an accurate eye tracker to stabilize the photocoagulation beam at a particular site.

Successful prior art methods for tracking eye movements have evolved along two principal approaches. One early approach was to attach a tightly fitting contact lens to the surface of the eye, and to either attach a test object to the lens or to reflect an image from a front-surface mirror attached to the lens and through an optical system to produce an image of the fundus stabilized against eye movements. The degree of stabilization in opto-mechanical systems of this type is inherently limited by the slippage that occurs between the contact lens and the angular movements of the visual axis of the eye. Stabilization of this kind has been demonstrated to be insufficient for precise work.

A second procedure for image stabilization involves a two-component system, including a device for tracking the movements of the eye and a mechanism for moving the object or image proportionally. Historically, tracking eye movements in this manner involved following the movements of a contact lens attached to the eye, so that this method suffers the same limitation as the one first described.

The earlier efforts required accurately fitted individual lenses for each subject. Although the contact lens systems offer the best resolution of any system down to 10 arc sec, they do so in general at the sacrifice of range. They are normally applicable for the study of small eye movements. The expense and discomfort of the contact lens makes it a technique more suitable for use on a few subjects.

Another prior art class of instruments uses corneal reflections and reflections from other optical curvatures in the eye (Purkinje images), and measures translation, as well as rotation. However, these instruments track movements at the surface of the eye, and are less accurate for stabilizing an image at the back of the eye.

Recently, emphasis has been placed on tracking structures at the fundus. One fundus tracking method involves projecting a scanning pattern onto the eye fundus, and detecting the translational and rotational movements of the reflected pattern by means of high-speed correlation processing of the video signal. Scanning systems of this type have generally been "light starved". That is, the light intensity required to provide a good image signal-to-noise ratio exceeds acceptable retinal illumination levels. Furthermore, scanning systems require extremely regular and fast moving optical deflectors. As a whole these systems require complex electronic processing, limiting their response time.

OBJECTS OF THE INVENTION

Principal objects of the invention are therefore, to provide an electro-optical eye movement tracker for directing onto the fundus a light beam stabilized against eye movement, having improved response time, having improved accuracy, which uses a relatively low light level, which preferably illuminates only that portion of the fundus to be tracked, which contains few moving parts, and which provides a minimum of discomfort to the patient.

Other objects of the invention are to provide an electro-optical eye movement tracker which allows independent viewing of the fundus, which provides sampling of the reflected stabilized beam, which is reliable, and which provides the user with operational flexibility adapted to stabilize diverse diagnostic, treatment, measurement and observational instruments.

SUMMARY OF THE INVENTION

A device for tracking eye movements according to the invention includes a laser source which projects a tracking strip of light on the fundus, optics for producing an image of reflected light from the tracking strip (image strip) onto a detecting element, equipment for repeatedly and rapidly scanning the intensity profile of the image strip, and processing electronics for analyzing the scanned intensity profile and providing correction signals to direct the optical path of both the tracking laser beam and an additional diagnostic beam to a fixed position on the fundus. A subject is positioned with the eye to be illuminated placed in optical alignment with light deflectors so as to allow the maximal range of beam movement about a feature on the fundus, the image of which serves as a tracking target.

This device for tracking eye movement follows differential change in the position of a spatially variant intensity feature of the fundus. The fundus is illuminated by the tracking strip and the intensity feature is detected in the image strip. The position of the intensity feature is related to a reference mark relative to a position stationary with respect to the device. In particular, the image strip falls on a position-sensitive detector placed at the image plane. The image strip is scanned, either mechanically or electronically, to obtain scan data containing information of light intensity as a function of position. A preferred scanning technique electronically samples within the detector the electronic signals caused by the image light. Very accurate correction is achieved due to the scan rate, and the performance of an ophthalmic system using the tracker is not degraded, as the illumination intensity, and the resolution are neither determined nor limited by the detecting element.

The detecting element provides an electric signal whose amplitude is proportional to the magnitude of the light intensity of the image strip produced by illumination of a portion of the eye fundus by the laser source. The processing electronics interpret the electronically encoded intensity profile produced by the image strip at the detector, sense differential movement of the eye, and produce a control signal which is provided to the optical deflectors for correcting three laser beam position on the eye fundus. The image strip is scanned rapidly and repeatedly providing fast-response iterative correction of the beam position with exceptional accuracy.

Further preferred embodiments include one or more refinements, including electrical shaping of the control signal provided to the optical deflectors; an image intensifier to improve detected contrast and intensity level of the fundus image at the detection element; an image rotator for aligning an image fundus structure in a preferred orientation with respect to a detector scan direction; an optical viewing path; and correction magnitude setting circuitry within the processing device for adaptive selection of different magnitude correction signals corresponding to detected large and small eye movements.

A tracking laser source of specific wavelength is used providing maximal sensitivity and minimal interference or distortion from the diagnostic beam, with good image contrast of the intensity feature and the surrounding background. The image strip of the tracking laser source is separated from the diagnostic laser source by selected filters and pupil arrangements.

DESCRIPTION OF THE DRAWINGS

These and other objects, features, and advantages of the invention will appear from the following description of preferred embodiments of the invention, taken together with the drawings.

DESCRIPTION OF ILLUSTRATED EMBODIMENT

The light stabilization device according to the invention will be understood by reference to a detailed description for a presently preferred embodiment of the stabilization device incorporated in an optical illumination instrument which aims a treatment beam of light at the fundus, which, illustratively, is shown as a helium-neon 632.8 nm red laser light beam.

Figure 1:
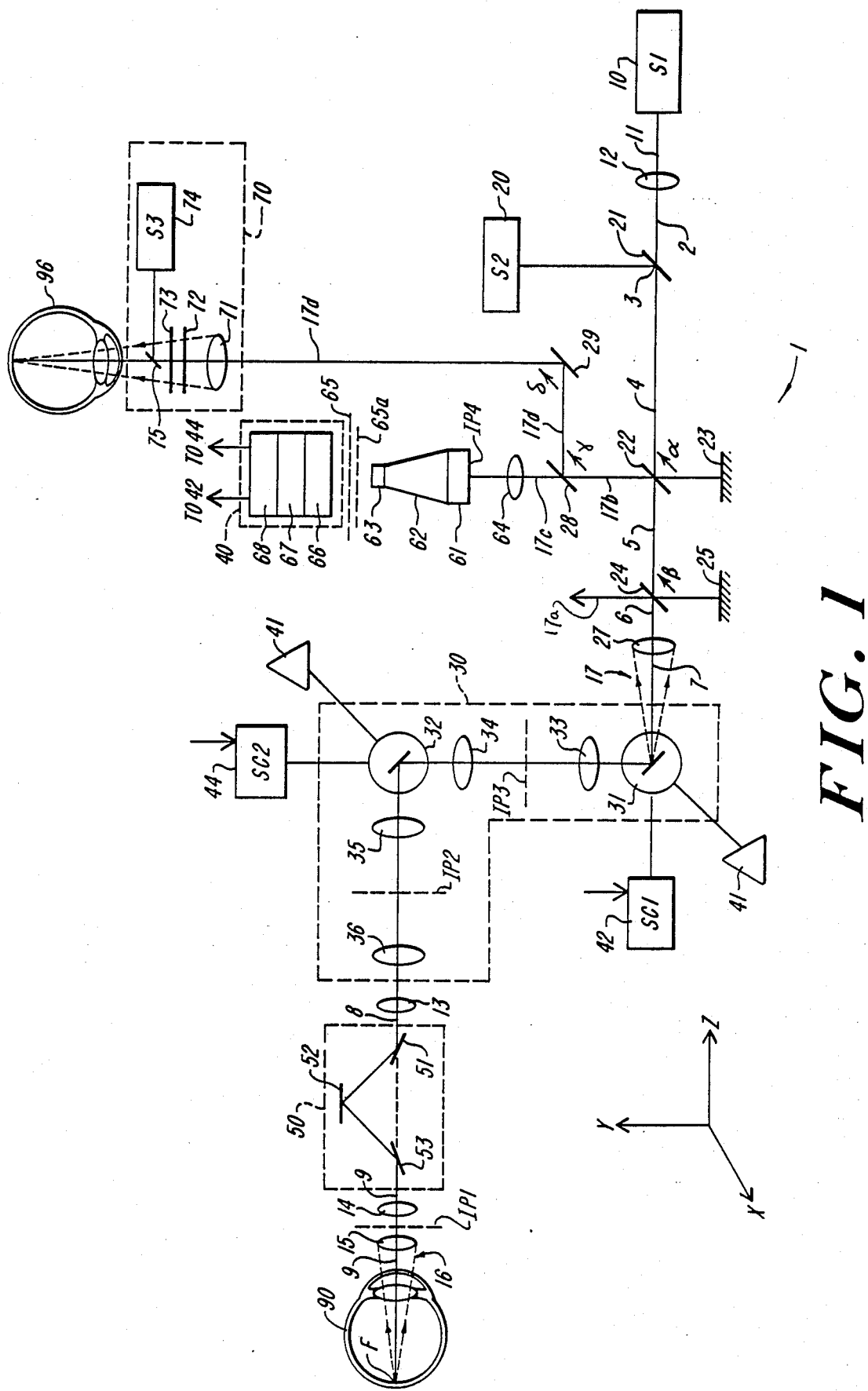
FIG. 1 is a diagrammatic representation of an eye movement tracker according to the invention and showing the optical light path from the laser sources to the subject's eye and from the subject's eye to the detecting element and observer's eye.

Referring to FIG. 1, a device 1 which follows eye fundus movement according to the invention has a green (543.5 nm) laser energy illumination source 10 which produces a narrow, slightly divergent, highly directed light output beam 11. Light output beam 11 passes through beam shaping optics 12 which attenuate the beam to an acceptable eye irradiance level and produce a preferably rectangular beam 2. A second laser source 20 produces a red beam which is folded into the beam path 2 at point 3 by means of a fifty per cent deflection element 21 to produce a combined beam 4 in which the two laser beams are coaxial and traverse substantially overlapping optical paths to the subject's eye. The locus of points containing these two beams is denoted as virtual pupil P1. The positions, within the optical setup, of laser sources 10 and 20 may be interchanged. The combined beam 4 encounters a fifty per cent deflection element 22 whereby fifty per cent of its intensity is deflected an angle $\alpha$ and stopped at optical absorber 23, and fifty per cent is transmitted along beam path 5. The transmitted light beam along path 5 encounters a red dichroic filter 24. Ninty-nine per cent of the red component and fifteen per cent of the green component of beam 5 are deflected an angle $\beta$ and stopped at optical absorber 25. The transmitted light beam 6 passes through an achromatic lens 27 which corrects for the natural divergence of the combined output beam 6 and produces a slightly convergent beam 7.

Beam 7 enters a two-dimensional image stabilization subsystem 30 indicated by the dashed line. The preferred system includes two open loop iron-core galvanometer scanners 31 and 32 oriented orthogonally with their planes of angular deflection coincident with the xy and yz system planes, respectively. Both galvanometers 31 and 32 are controlled by signals from a processing device 40 during an automated iterative correction sequence described below. The control signals to the galvanometers are shaped to minimize oscillations in the mirror position after rotation, in a manner known in the scanning control art. A joystick 41 is also attached to the processing controller which produces mirror control signals for manual control of the mirror position. Galvanometer scanning assemblies such as those manufactured by General Scanning of Watertown, Massachusetts are suitable for driving and controlling the positions of the mirrors. Lenses 33, 34 between the galvanometers position the axis of rotation of each scanner mirror at the center of rotation of the virtual eye image, as discussed below.

Beam 7 is deflected by galvanometer-controlled mirror 31, passes through lenses 33 and 34, and is deflected by galvanometer 32. It then passes through lenses 35 and 36 to exit the stabilization subsystem 30 as a deflected beam 8. The emergent beam 8 passes through lens 13 and into an image rotator 50. Within image rotator 50 the beam is reflected by adjustable front-surface mirrors 51, 52 and 53 and emerges from the image rotator as beam 9 along a path collinear with beam 8. The beam 9 passes through lens 14 and ophthalmoscopic lens 15, enters the eye and strikes the fundus F. The fundus scatters a portion 16 of the incident light to exit from the interior of the eye through the pupil. The scattered light travels back through the ophthalmoscopic lens 15 and forms an image at image plane IP1 which in turn is imaged by lens 14 onto adjustable mirror 53 of image rotator 50. The scattered beam 16 is reflected out of the image rotator by mirror 51 and passes through lens 13. Lenses 13, 36 and 35 image the fundus in planes IP2 and IP3, both of which are conjugate to the subject's fundus. The reflected beam passes through the two-dimensional image stabilization subsystem 30 and emerges as a divergent beam 17. A lens 27 converges beam 17. At dichroic filter 24 the red component of the reflected beam is ninety-nine per cent deflected an angle $\beta$ emerging at the diagnostic output port as a beam 17a. The green component of beam 17 is eighty per cent transmitted by a filter 24 and fifty per cent deflected by an angle $\alpha$ by a deflector 22 to produce a return tracking beam 17b. Beam 17b strikes a green dichroic filter 28. Eighty per cent of the green component of beam 17b is transmitted through filter 28 emerging as a beam 17c, and the remainder is deflected an angle $\gamma$ as a residual return beam 17d.

Beam 17c enters an image intensifier subsystem 60 indicated by the dashed line. One preferred intensifier system includes an image intensifier tube 61 coupled by a fiber optics minifier 62 to a two-dimensional charge-coupled device (CCD) 63. Image intensifiers such as those manufactured by ITT's electro-optical division of Roanoke, Virginia are suitable for this low intensity imaging application. The CCD transmits electronically, serially encoded light intensity as a function of spatial information to an output processor 40. A lens 64 forms an image IP4 of beam 17c on the photocathode of the image intensifier tube 61. The image intensifier amplifies the intensity of the fundus image IP4 with a spatial resolution comparable with that of the CCD. The fiber optics minifier couples the light output of the image intensifier to the charge-coupled device 63, which has an active surface several millimeters square, while increasing the spatial resolution by reducing the size of image IP4. The illustrated fiber optic minifier employs a coherent tapered fiber bundle which permits the quality reduction of high resolution images. One manufacturer of minifiers is Galileo Electro-Optics of Sturbridge, Massachusetts. For the CCD, charge-coupled devices and supporting electronics such as those manufactured by Fairchild of Palo Alto, California are suitable for this application requiring electronic encoding of two-dimensional intensity profiles.

The CCD 63 converts the photo-signal to an analog electrical signal which is clocked into the processing device 40. The processing device analyses this electrical signal, and provides a correction signal via scanner control 42, 44 which repositions the front-surface mirrors of galvanometers 31, 32 and hence repositions the incoming combined treatment/tracking beam 7 on the eye fundus at F.

Beam 17d deflected from filter 28 encounters a front-surface mirror 29, is reflected by an angle δ and enters an optical viewing subsystem 70. The optical viewing subsystem contains a lens 71 for focusing the image of the eye fundus F on the retina of the observer's eye 19. Two filters 72 and 73 together produce a narrow bandpass filter passing yellow optical illumination light which is provided by an optical illumination source 74. A small turning mirror 75 injects the yellow observation beam along the reverse of the optical path just described to the subject's fundus for observation illumination.

As described in more detail below, apparatus according to the invention produces a signal at the two-dimensional charge-coupled device 63 with a signal-to-noise ratio which is comparatively high, especially considering the high turbidity of the media within the eye through which the optical tracking energy must pass. The contrast of spatially variant intensity features of which the apparatus is designed to follow is preferably optimized by employing the tracking laser light source in combination with a small-aperture collection pupil, thus reducing signal degradation due to scattered light.

In the above described apparatus, the laser light sources 10 and 20 are selected to serve distinct purposes. Source 10 provides a small strip of laser light which is directed onto a particular retinal structure, the image of which is tracked to provide eye-motion correction signals. Preferably, the tracking source 10 is a green helium-neon laser from which energy is available at a single power level with wavelength 543.5 nm. Green light is useful both for examining the superficial layers of the eye fundus, and for providing high contrast demonstration of the retinal vasculature, retinal pigment epithelium, and the choroidal vessels in less pigmented peripheral fields. There are no operational requirements on the intensity or wavelength of laser source 20, provided the wavelengths from sources 10 and 20 are physiologically safe and spectrally separable. For the purpose of illustration, the diagnostic beam is provided by a red helium-neon laser source 20. The invention provides a stabilizer for a wide variety of fundus-illuminating instruments; for other sources, different filters may be substituted in the optical path.

Figure 2:
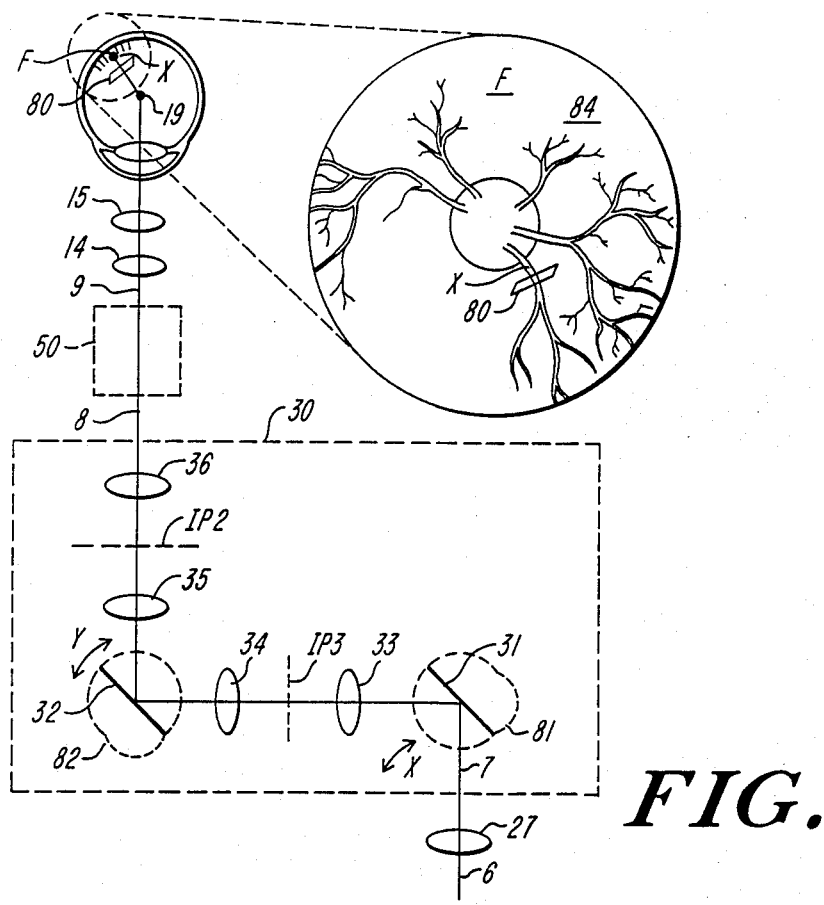
FIG. 2 shows the optical arrangement of the beam steering mechanism.

The geometry and alignment of the tracking assembly will be understood with reference to FIG. 2. The source beam 10 is positioned on a retinal structure of choice (denoted by X) by joystick 41 which manipulates the galvanometer-controlled mirrors 31, 32. Magnified detail view 84 shows the strip 80 positioned on a vessel denoted X of the fundus F. Once the structure X is centered in the green tracking strip 80 of the laser source 10, activation of the automated iterative correction procedure is initiated by pushing a mechanical push button switch on the joystick. Both laser light sources 10 and 20 follow a coaxial optical path to the eye fundus, so that corrections made to the position of the beam originating at source 20 are coincident with corrections made to the beam originating from source 10. That is, corrective motions of mirrors 31, 32 redirect the common optical path followed by the combined beam, formed by tracking source 10, treatment source 20 and observation source 74, discussed above. In FIG. 1 the two beams from sources 10, 20 are referred to collectively as a single beam, starting at position 4. Source 20, the diagnostic beam, is thus stabilized on the eye fundus F. It will be appreciated that source 20 need not produce a beam but, as discussed more fully below, may produce a pulsed or continuous pattern of illumination which is directed along the common path. More generally, the eye tracker of this invention achieves two-dimensional stabilization of an arbitrary light stimulus pattern at the eye fundus position. The stimulus pattern can be offset by an arbitrary angle from the tracking target structure of the fundus without compromising its stability characteristics.

Still referring to FIG. 2, the two-dimensional path corrector of the presently preferred image stabilizing system is shown in relation to the subject's eye. The fundus of the subject's eye F is imaged in planes IP2 and IP3, both of which are conjugate to the fundus. The optical system contains two open loop iron-core galvanometer-controlled mirrors 31 and 32 that rotate in response to signals from the processing device 40. The two mirror axes of rotation are mounted orthogonally along the x- and y-axes of the overall coordinate system. In the plane of each axis of rotation is a virtual image of the center or rotation 19 of the eye, illustrated by virtual eye images 81 and 82. When the galvanometer-controlled mirrors are driven by the appropriately scaled correction signals, they redirect the optical path so as to compensate for the subject's normal eye movements. The orthogonal orientation of the mirrors provides stabilization in two dimensions to keep the tracking strip 80 directed on a fixed target on the fundus and to keep the image of the targeted fundus structure aligned in a fixed position on CCD 63. The imaging optics include two high quality relay-lens pairs 33, 34 and 35, 36 with the lens pairs separated by twice their focal length.

Optimal positioning of the image of the tracking target is achieved as follows. First, the tracking strip is directed at the fundus and a suitable tracking target is identified in the small region illuminated by the strip, which region may be, for example, a rectangular area of approximately one by five millimeters. The long axis of the strip serves as a direction-indicating marker which is visible on a macroscopic level to facilitate the setting up. The tracking target preferably includes two linear vessels which are spaced close to each other and oriented substantially orthogonally, with one vessel parallel to the length or width of the strip. The image rotator is then rotated to align the long axis of the tracking beam with a scan line (e.g. with the length dimension) of the CCD, so that the images of the two vessels cut across the orthogonal scan lines (or extensions thereof) of the CCD. The joystick is then used to "steer" the tracking beam (hence, also the image of the tracking structure), so that the two linear vessels move to a position such that one vessel cuts perpendicularly across each scan line on the face of the CCD. In this position the scanning planes of the galvanometer-controlled mirrors are aligned with the x-y coordinates of the CCD, maximizing the sensitivity of the tracker to eye motion, and minimizing the chance that a large rapid eye movement will remove a targeted vessel or other spatially variant intensity fundus structure from the field of scan.

A number of image rotating devices are known; the preferred embodiment consists of three front-surface mirrors arranged in the configuration illustrated in FIG. 1. A surface reflecting device is preferred to an internally reflecting device such as a Dove prism because the light loss of a surface reflecting device is less. As shown in FIG. 1, the rotation axis of the image rotator 50 coincides with the optical axis of the apparatus.

In addition to beam alignment, the detection of fundus illumination requires some care. The strip of green light produced by laser source 10 is referred to as the "tracking strip" when shown on the fundus, as distinguished from the "image strip" which is the green light exiting the eye and producing an image of the tracking strip at the front surface of the position-sensitive charge-coupled device 63.

Light is scattered from the eye fundus F in all directions. The low light levels permitted for illumination of the retina are attenuated further within the eye, resulting in an image strip which is close to the intensity threshold of available position-sensitive semiconductor detectors. The position-sensitive detector electronically scans the image strip and provides an analog signal containing spatially resolved intensity information to the output processor 40.

Of the three commercially available position-sensitive semiconductor devices CCD, CID, and Reticon diode array, the CCD was chosen for its low noise characteristics during low-light level illumination. The CCD is a charge-transfer device which permits the movement of packets of photo-induced electrons from one location in its silicon substrate to another without losing spatial information. The spatial resolution of such devices is approximately 13 μm. Such devices have a linear response over several decades of light intensity. At low light levels the device is preferably cooled to reduce thermal noise and to improve the signal-to-noise ratio.

A CCD contains many photo-active sites physically separated and electronically isolated in a dense array. In this invention a two-dimensional array is specified. The photo-active sites convert the incident photons into electronic signals which are subsequently serially clocked out. Each site contributes a packet of electrons separated from adjacent packets in time, and a charge-to-voltage amplifier converts the charge signal into a voltage modulated signal with voltage amplitude representing light intensity, and its variation in time providing spatial information. For clarity of illustration, the CCD is treated here as a black box requiring at its input a spatially resolved image of sufficient intensity and producing at its output an electronic signal containing spatial and intensity information of the input.

The low intensity backscattered green image strip is close to the intrinsic noise level, and the image strip intensity is preferably increased by directing the two-dimensional image strip onto the photocathode of an image intensifier (61, FIG. 1), which provides a spatially resolved reproduction of the original image at a far higher intensity. The intensified output of the image intensifier couples via a fiber optics minifier 62 to the front surface of the CCD 63. The signal-to-noise ratio of the CCD is further enhanced by attaching to its back surface a Peltier effect thermoelectric cooler 65 which maintains the CCD at a temperature below ambient. The thermoelectric cooler 65 generates a magnetic field which interferes with the proper operation of the CCD 63. To permit shielding against this effect, a suitably thick copper heat conductor 65 connects the two devices a short distance apart, and a thin sheet of mu metal magnetic shielding (not shown) is then placed between them to block magnetic fields.

To track eye movement, a presently preferred processing method samples the image strip intensity distribution along two orthogonal lines (x- and y-scan lines) each consisting of a single row of pixels.

Figure 3:
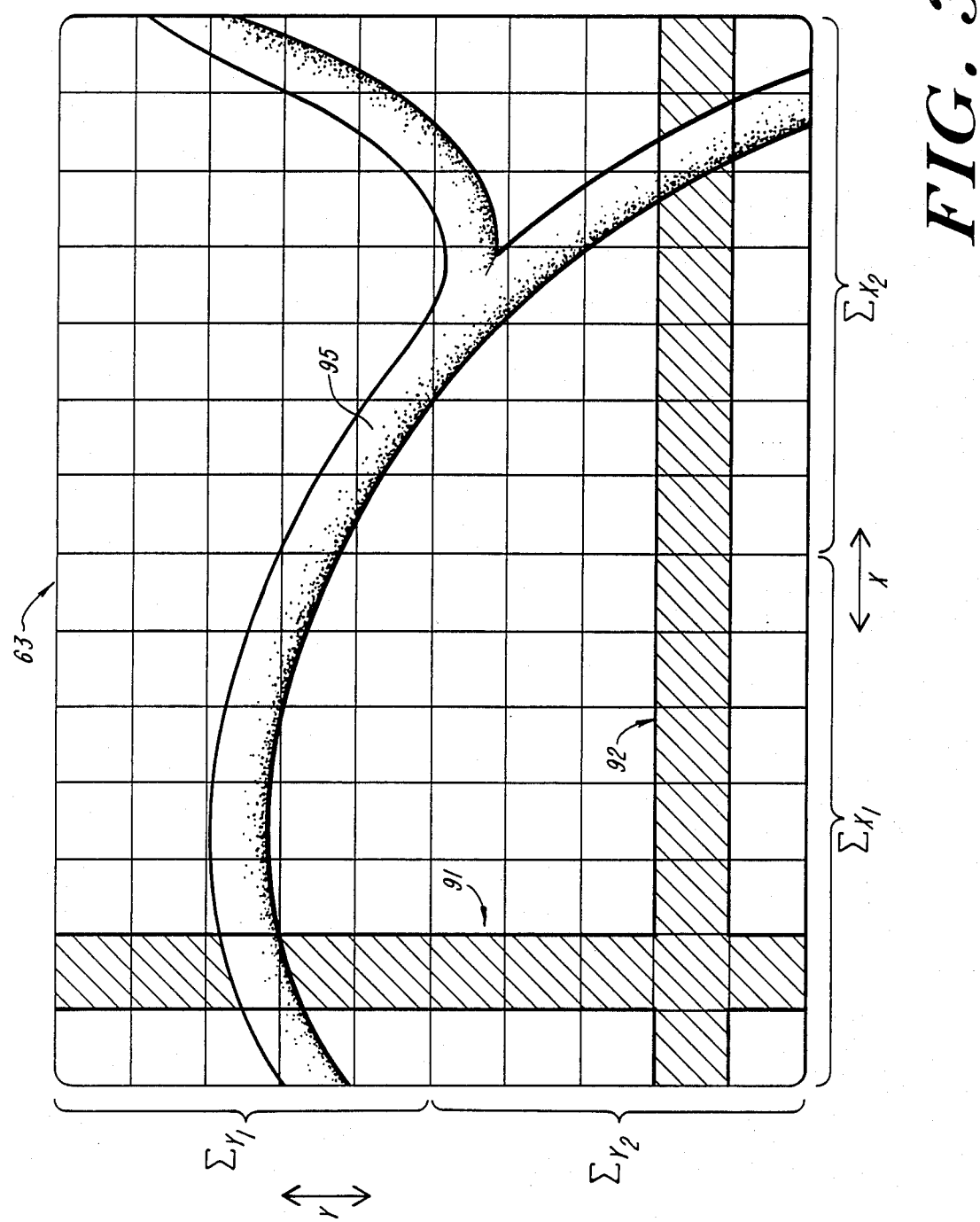
FIG. 3 illustrates the motion tracking of an imaged fundus structure.

FIG. 3 illustrates the tracking of the illustrated embodiment and shows one suitable orientation of the image strip on the face of CCD 63. Two orthogonal scan lines 91, 92 touch only at one end, and preferably to maximize their length they form half the perimeter of the rectangular two-dimensional CCD 63. For purposes of illustration, the number of spatial cells (pixels) illustrated is substantially less than the actual number of the CCD. An intensity feature, e.g., a retinal vessel 95 is chosen such that one portion of the retinal vessel image intersects the x scan line 92 and one portion intersects the y scan line 91, preferably crossing the scan lines at right angles. This selection of an intensity feature and positioning within the tracking strip is accomplished using the joystick and image rotator as described above, and is done in a manner which ensures only one intensity extremum per scan line field. The system magnification and the CCD area are such that a single vessel intersects each scan line, and there is no other vessel in the field which might cause the tracker to jump to a different target. The tracking strip is aimed such that the image of a blood vessel intersects each scan line once, and only one blood vessel crosses each scan line. Once the desired orientation is achieved with the image rotator, and the position is set using the joystick, pressing the push button switch on the joystick 41 locks the extrema positions along the scan lines into memory. Thereafter the processor 40 scans the photodetector and detects eye movement by tracking the change in position of the imaged vessel.

By employing a continuous tracking beam which illuminates a region of the fundus, and electronically scanning a fixed photodetector array, the illustrated system achieves a scan rate of 1000 or more complete image strip scans (frames) per second. The electrical processing portion 40 includes timing, memory processing, and control sections 64, 67, 68 discussed below. The clock rates and timing required to achieve the 1000/sec scan rate are known in the photosensing art and are provided by timing and synchronization circuit 66. The electronic signals proportional to the light intensity for each one of the pixels of the charge-coupled device are serially applied to a memory processing and storage circuit 67. Circuit 67 stores an active two-dimensional array of the electronically encoded intensity profile, refreshing each memory location as new pixel data arrives. The memory processing circuit 67 also selects the two orthogonal lines of pixel data, preferably intersecting at one corner of the CCD as described above. These two lines coincide with the x- and y-axes of the overall coordinate system and are referred to as the x- and y- scan lines, respectively. The x- and y- scan lines are treated independently. Position information is encoded as a differential. The intensity profile of each scan line is summed over two half-scans yielding $\Sigma x_1$, $\Sigma x_2$, for the x-scan line, and $\Sigma y_1$, $\Sigma y_2$ for the y-scan line. During the automated iterative correction sequence the ratio $\Sigma x_1/\Sigma x_2$ and the ratio $\Sigma y_1/\Sigma y_2$ are preserved by controlling the galvanometer mirrors to redirect the tracking beam. For each of the two scan lines processing circuit 67 sums the first half of the total pixels per line ($\Sigma_1$), and compares this value with the sum of the second half of pixels from the previous frame ($\Sigma_2$). Control circuit 68 generates a unit step in the position of the appropriate galvanometer in response to a change in $\Sigma_1/\Sigma_2$. The direction of the step depends on whether the previous frame sum $\Sigma_2$ is greater than or less than the present inferred frame sum $\Sigma_2'$.

In the preferred embodiment, circuit 68 includes a variable step setting circuit for providing coarse, medium and fine corrections to the beam position, so as to achieve a smoother, more continuous tracking action. This adaptive control signal magnitude setting is preferably accomplished by a configuration of resettable counters in software.

Figure 4:
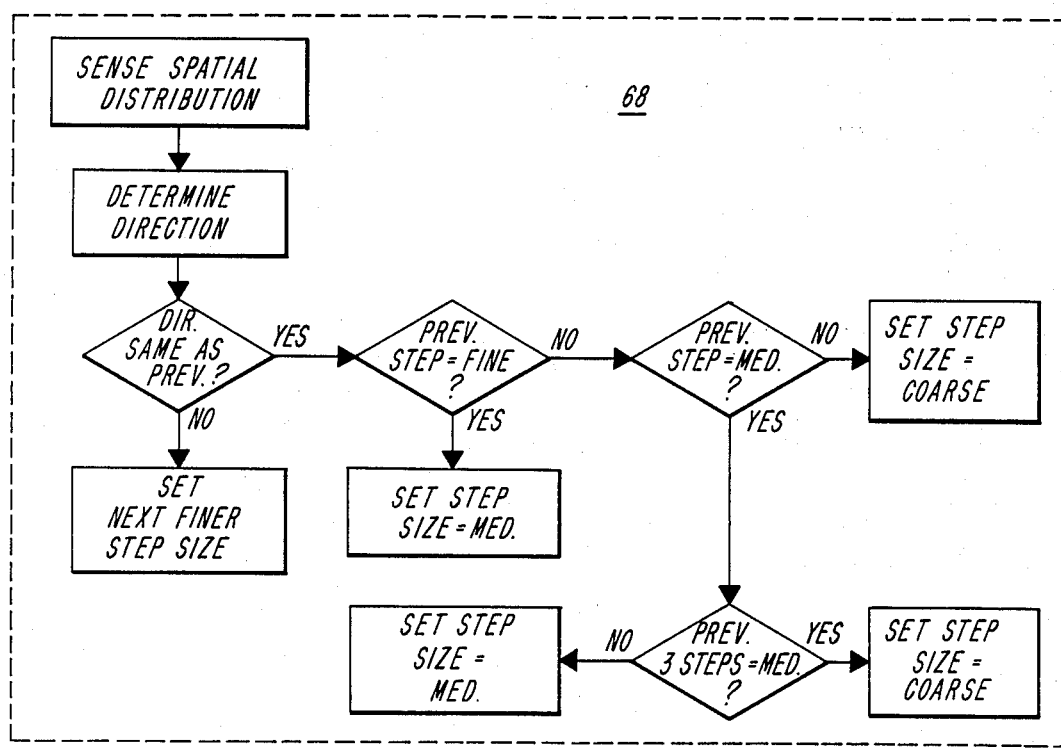
FIG. 4 is a flow chart illustrating adaptive motion tracking according to a preferred embodiment of the invention.

FIG. 4 shows a flow chart for the step size correction signal determination according to this aspect of the invention. The step size of the control signal applied to the galvanometer mirror adaptively varies from coarse step size to fine step size dependent upon the history of previous corrections. The size of the unit step takes one of three values depending on the state of the circuit 68. If two successive steps in one direction have been recorded, circuit 68 changes state from fine step (1 $\mu$m) to medium step (10 $\mu$m), and if four successive steps in one direction have been recorded during the medium step mode, circuit 68 changes state to coarse step mode (25 $\mu$m). A change in direction causes an interruption of the successive step count corresponding to a particular state and resets circuit 68 to the next lower state, resulting in a finer step size. During the action of the circuit 68 which sends the correction signals to the x- and y-galvanometers, the circuit 67 continues to sum the remaining pixels of the current scan frame. Within the time it takes for the sum to be completed, the galvanometer has completed adjustment of both x and y galvanometer-controlled mirrors. The system subsequently begins another scan.

A third, optional, portion of the stabilization system is the optical viewing subsystem, illustrated in FIG. 1. The optical viewing subsystem 70 provides both a port for viewing an optical image of the subject's eye fundus, and a means for illumination 74. The optical path defining and imaging optics discussed above provide a thirty degree viewing field. White illumination light enters the optical viewing system 70 from source 74 and passes through the narrow band-pass filters 72 and 73. The system is constructed such that each of the light sources 10, 20, and 74 are spectrally separable. For this reason the light emerging from filters 72 and 73 in the illustrated embodiment is yellow. The yellow illumination light enters the main beam path at fifty per cent deflector 22, follows the optical path to the fundus F of the subject's eye 90, and returns to the optical viewing port along the reverse path for viewing by an observer's eye 96. Transmission at dichroic filter 24 and reflection at dichroic filter 28 ensure that the illumination light does not interfere with the more sensitive function of the tracking subsystem 60 or contaminate the diagnostic beam 17a at the instrument output port.

It will be appreciated that although the eye fundus tracker of the invention has been described with reference to an instrument having a narrow source 20 projecting a beam which is to be stabilized on the fundus, which may be, for example, a xenon or laser photocoagulator, such illumination instrument is by way of illustration only, and not limitation. Numerous other illumination instruments for illuminating the fundus are presently limited in their applications due to eye movement, and the invention includes an eye fundus tracker adapted for stabilizing illumination of any such instruments, and systems having the combination of any such instrument with an eye fundus tracker as described herein. Examples of such illumination instruments are Doppler velocimeters for measuring retinal blood flow characteristics, image or pattern projecting apparatus which project an image onto the fundus for performing psychophysical research on vision, laser photocoagulators, scanning laser microscopes and other instruments, which by their nature, require very precise light stabilization on the fundus.

The invention being thus disclosed, other embodiments of the invention including additions, subtractions, deletions, or modifications of the disclosed embodiment will occur to those skilled in the art, and are within the scope invention, as defined by the following claims.

What is claimed is:

1. Apparatus for directing a first beam of light energy onto the fundus of an eye and for stabilizing the beam during eye movement, such apparatus comprising means defining an optical path to the fundus for directing a first beam of light energy to be stabilized on the fundus, means for producing and directing at the fundus a tracking beam of light energy, distinct from the first beam, for illuminating a region surrounding a microscopic tissue feature constituting a narrow tracking target extending along a line, angular correction means responsive to a control signal for controllably redirecting the optical path to the fundus, imaging means for focusing light reflected from the fundus through the angular correction means so as to form a fundus image including an image of the tracking target, alignment means in the optical path for aligning the image of the tracking target to place said line in a selected position, and tracking means responsive to movement of the image of the tracking target transverse to said line for developing a control signal representative of eye movement, said control signal being provided to said angular correction means to redirect the optical path so that the first beam is stabilized on the fundus in a fixed position during eye movement.

2. Apparatus according to claim 1, further comprising a photosensor array for developing an electronic output signal indicative of spatially distributed light energy impinging thereon, and wherein said imaging means forms an image of a region of the fundus including the tracking target on said photosensor array.

3. Apparatus according to claim 2, wherein the tracking means further comprises
electronic scanning and processing means for electronically scanning said photosensor array so as to develop a feature signal representative of the tracking target position, and
comparing means for comparing the feature signal at successive times so as to develop said control signal.

4. Apparatus according to claim 3 further comprising an image intensifier between said imaging means and said photosensor array.

5. Apparatus according to claim 3 adapted for tracking a blood vessel target, wherein said tracking beam is a green light beam for enhancing contrast of a target image, and wherein said alignment means includes an image rotator for rotating the image to align it orthogonal to a scan direction of said scanning means.

6. Apparatus according to claim 1, wherein the apparatus is an ophthalmic instrument further comprising means for producing said first beam of light energy with a wavelength distinct from the tracking beam.

7. Apparatus for directing a first beam of light energy onto the fundus of an eye so that the beam strikes the eye at a fixed position during eye movement, such apparatus comprising
means defining an optical path to the fundus for directing a first beam of light energy to be stabilized on the fundus,
means for producing and directing at the fundus a second beam of light energy,
angular correction means for controllably redirecting the optical path so as to controllably aim the first beam at the fundus,
imaging means in the optical path for focusing through the angular correction means light of the second beam reflected from the fundus, so as to form a fundus image,
a photosensor array for receiving the image of a selected portion of the fundus including a microscopic target structure having a characteristic luminance and extending along a line of elements of the array, and for developing an electronic output representing such image, and
means for electronically tracking the imaged target structure by processing the electronic output so as to develop a tracking signal representative of eye movement transverse to said line of elements,
said tracking signal being provided to said angular correction means so that the optical path is redirected to maintain the image of the target structure in a fixed position on the photosensor array, thereby stabilizing the first beam on the fundus.

8. In an ophthalmic imaging or treatment device of the type which includes optical path defining means for directing or receiving illumination along an optical path to the eye fundus, the improvement comprising a stabilizer for maintaining the optical path directed at a fixed fundus position, such stabilizer including
means for producing and directing at the fundus a tracking beam of light energy,
angular correction means in the optical path for controllably redirecting the optical path to the fundus,
imaging means for focusing through the angular correction means light reflected from the fundus so as to form a fundus image,
alignment means in the path for moving the image of the fundus to align in a selected position an image of a fundus structure having a characteristic luminance and extending along a line,
means for tracking motion of the image of the fundus structure transverse to said line so as to develop a signal representative of eye movement, and
means for controlling the angular correction means in accordance with said signal to move the optical path by a fixed amount in a direction opposite to said motion, said tracking and controlling means being actuated at a rate greater than fifty times per second so that the optical path intersects the fundus in a stabilized position.

9. A stabilization system for an ophthalmic illumination instrument, such system comprising
means defining an optical path for conducting to the fundus illumination of the ophthalmic illumination instrument,
means for producing and directing at the fundus a tracking beam of light energy for illuminating at one time a region about a microscopic tracking target of fundus tissue,
angular correction means responsive to a control signal for controllably redirecting the optical path to the fundus,
imaging means for focusing light reflected from the fundus, back through the angular correction means so as to form a fundus image including an image of the tracking target which extends along a line,
alignment means in the optical path for aligning the image of the tracking target to place said line in a selected position, and
tracking means responsive to movement of the imaged tracking target for developing a control signal representative of eye movement transverse to said line, said control signal being provided to said angular correction means to redirect the optical path whereby the illumination from the ophthalmic instrument is stabilized on the fundus in a fixed position during eye movement.

10. Apparatus according to claim 9, wherein
said angular correction means includes first and second galvanometer-controlled front-surface mirrors mounted for pivotal motion about respective first and second orthogonal axes for controllably redirecting the optical path in two dimensions, and wherein said tracking means includes a photodetector for generating a spatially resolved electronic signal representative of said image, and further includes scanning and processing means operative on said spatially resolved signal for determining said control signal.

11. Apparatus according to claim 10, wherein said processing means comprises
means for summing the spatially resolved electronic signals from the photodetector over a selected group of spatial elements and for providing a movement signal representative of movement of an imaged fundus structure in two orthogonal directions, and step control means responsive to plural movement signals for providing a selected magnitude step correction signal as the control signal to the first and second galvanometer-controlled mirrors.

12. Apparatus according to claim 10, further comprising a lens system positioned with respect to the two galvanometer-controlled mirrors such that the fundus of the subject's eye is imaged in two planes, each of which is conjugate to the subject's fundus, and further such that the nominal plane of the axis of rotation of each galvanometer-controlled mirror contains a virtual image of the center of rotation of the subject's eye.

13. Apparatus according to claim 10, including first and second galvanometer drive members for rotating said first and second mirrors respectively, said first and second drive members being responsive to said control signal.

14. Apparatus according to claim 9, wherein the tracking means further includes means for adaptively determining a control signal magnitude as a step-signal which varies in accordance with the magnitude and direction of at least one previous control signal and with the movement of the imaged tracking target.

15. Apparatus according to claim 9, wherein said instrument illumination and said tracking beam are coaxial along a portion of said optical path including said angular correction means, and lying between a beam junction point and the eye.

16. Apparatus according to claim 9 wherein said angular correction means comprises means for deflecting along two orthogonal axes said light beams traveling in forward and reverse directions on the optical path.

17. Apparatus according to claim 9, wherein said alignment means comprises
    a low-loss front-surface mirror optically aligned with an image of the eye fundus for angularly rotating the image of the tracking target.

18. Apparatus according to claim 9 further comprising
    means for providing observation illumination, and
    optical filter means for separating reflected light from the eye fundus into three components corresponding to
    (i) said tracking beam;
    (ii) said illumination from the instrument; and
    (iii) said observation illumination
    so as to separately divert said three light components to the image intensifier, to a diagnostic beam output port, and to an optical viewing system, respectively.

19. Apparatus for directing a first beam of light energy onto the fundus of an eye and for stabilizing the beam during eye movement, such apparatus comprising
    means defining an optical path to the fundus for directing a first beam of light energy to be stabilized on the fundus,
    means for producing and directing at the fundus a tracking beam of light energy for illuminating a microscopic tracking target on the fundus,
    angular correction means responsive to a control signal for controllably redirecting the optical path to the fundus,
    a photosensor array having a plurality of photosensitive surface elements for developing a two dimensional spatially resolved electronic signal representative of light energy impinging on a surface of the array,
    imaging means for focusing through the angular correction means light reflected from the fundus so as to form a fundus image on the photosensor array, such image including an image of the tracking target,
    means for aligning the image of the tracking target in a selected position across a line of photosensitive elements on said photosensor array, and
    tracking means responsive to movement of the imaged tracking target for electronically scanning the spatially resolved electronic signal so as to develop a control signal representative of eye movement, said control signal being provided to said angular correction means to redirect the optical path so that the first beam is stabilized on the fundus in a fixed position during eye movement.

20. Apparatus according to claim 19, wherein the means for aligning includes an image rotator.

21. A method of stabilizing an optical instrument on a selected region of the fundus of an eye of a subject, wherein the optical instrument is aimed at the fundus along a path including an optical steering system, such method comprising the steps of
    (i) directing a tracking beam to illuminate a microscopic tissue structure serving as a target feature on the fundus,
    (ii) imaging the target feature through the steering system across a line of sensing elements of a photosensor array,
    (iii) scanning the line of sensing elements of the photosensor array to detect motion of the imaged target feature along said line of elements, and
    (iv) developing control signals indicative of image motion and providing the control signals to the steering system for controlling the steering system to maintain the imaged target feature stationary, so that the instrument remains aimed at the selected fundus region.

* * * * *

UNITED STATES PATENT AND TRADEMARK OFFICE
CERTIFICATE OF CORRECTION

PATENT NO. : 4,856,891  
DATED : August 15, 1989  
INVENTOR(S) : Pflibsen et al.

It is certified that error appears in the above-identified patent and that said Letters Patent is hereby corrected as shown below:

Column 1,  
Line 3, the following two sentences should be inserted:  
-- STATEMENT OF RIGHTS  
This invention was made with government support under Grant EY 01303 awarded by the National Institutes of Health. The Government has certain rights in the invention. --

Signed and Sealed this

Twenty-first Day of October, 2003

JAMES E. ROGAN  
*Director of the United States Patent and Trademark Office*